United States Patent [19]

Lingertat et al.

[11] Patent Number: 4,985,025
[45] Date of Patent: Jan. 15, 1991

[54] ADHESIVE CLOSURE SYSTEM FOR DISPOSABLE DIAPERS

[75] Inventors: Arnold Lingertat; Morris K. Swieringa, both of Bucks County, Pa.

[73] Assignee: McNeil-PPC, Inc., Milltown, N.J.

[21] Appl. No.: 824,928

[22] Filed: Jan. 31, 1986

Related U.S. Application Data

[63] Continuation of Ser. No. 562,906, Dec. 19, 1983, abandoned.

[51] Int. Cl.⁵ ............................................. A61F 13/16
[52] U.S. Cl. .................................................. 604/390
[58] Field of Search ................................ 604/389, 390

[56] References Cited

U.S. PATENT DOCUMENTS

| | | | |
|---|---|---|---|
| 3,554,195 | 1/1971 | Murdoch | 604/390 |
| 3,848,597 | 11/1974 | Endres | 604/390 |
| 4,211,226 | 7/1980 | Schaar | 604/390 |

Primary Examiner—Stephen C. Pellegrino
Assistant Examiner—Sharon Rose
Attorney, Agent, or Firm—Lawrence D. Schuler

[57] ABSTRACT

An improved closure system for a disposable diaper is provided by directly securing pressure sensitive adhesive to exposed portions of the backing sheet and releasably retaining the closures in a storage position by detachably securing the pressure sensitive adhesive to release means inwardly of the pressure sensitive adhesive. The release means may be provided on the facing layer of the diaper, or on the backing layer thereof.

2 Claims, 1 Drawing Sheet

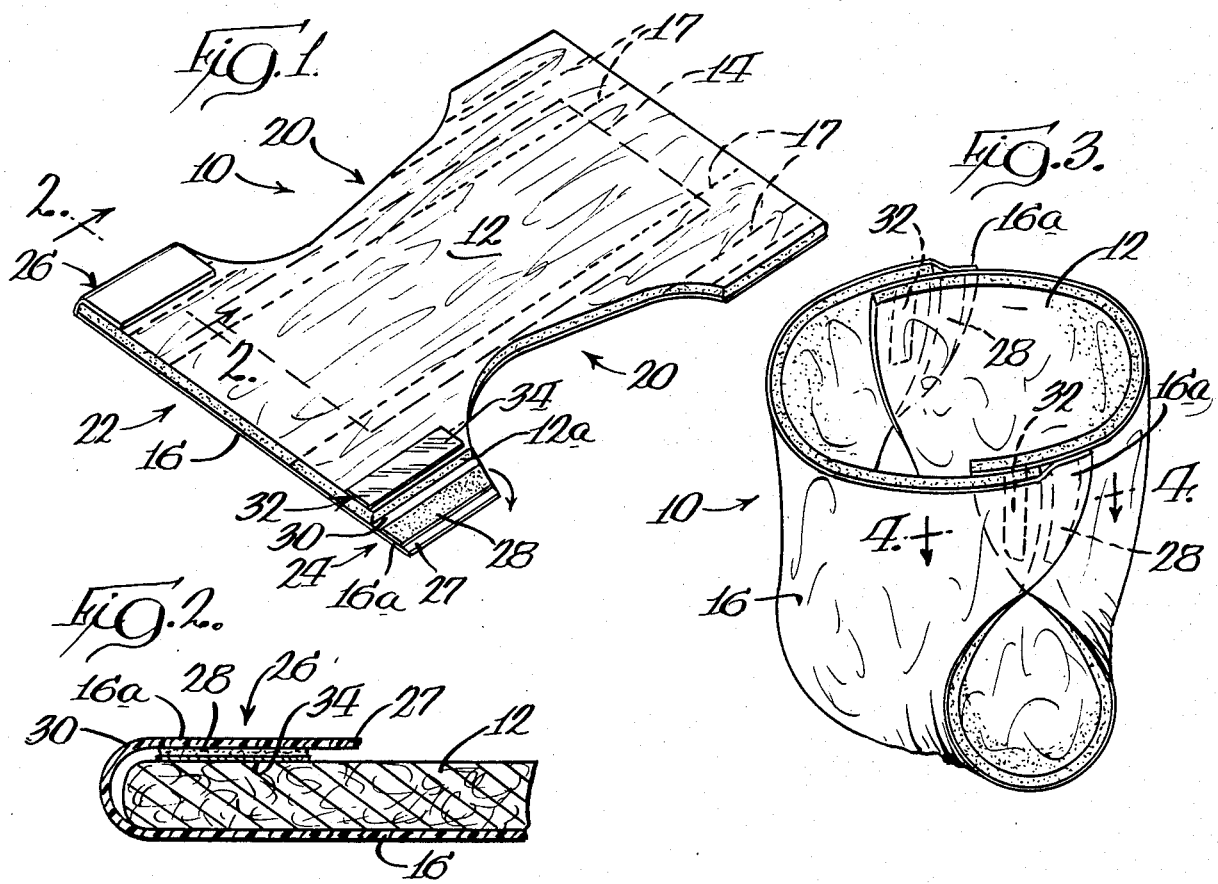
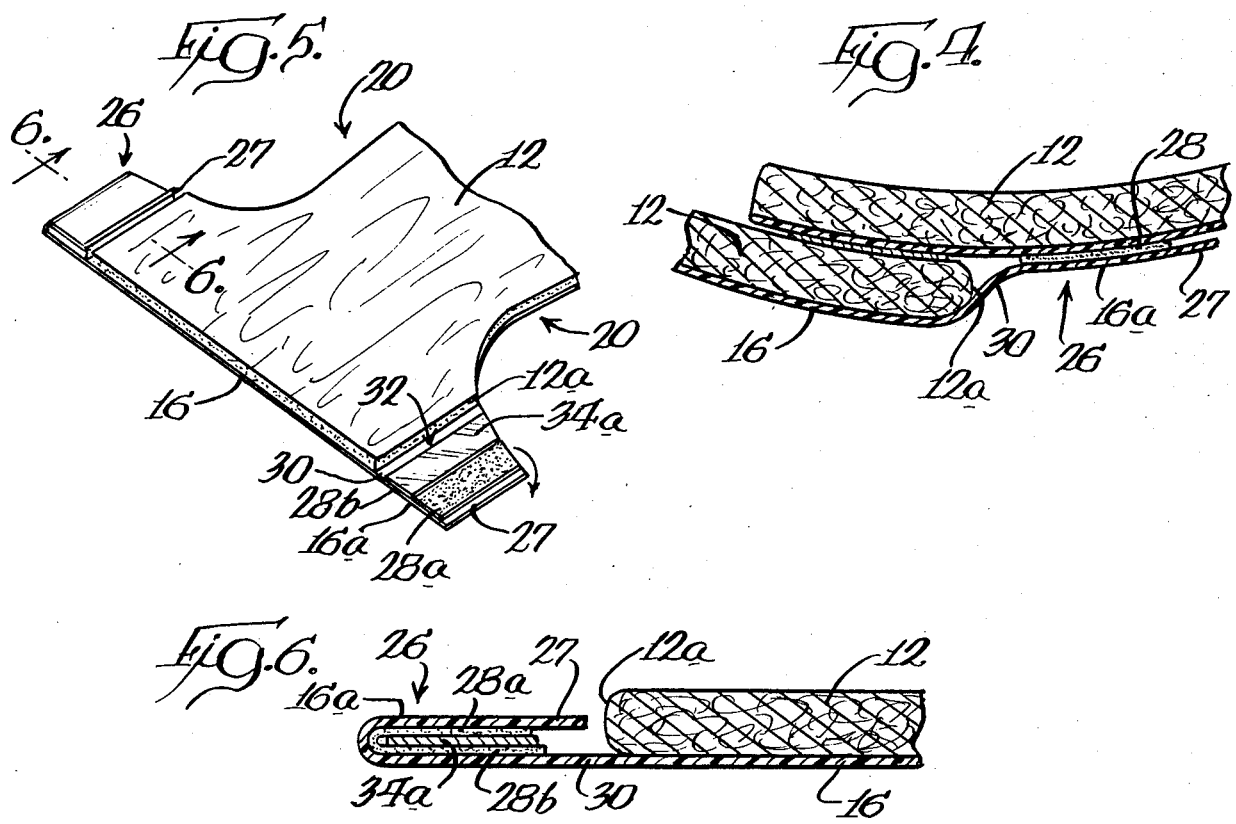

ADHESIVE CLOSURE SYSTEM FOR DISPOSABLE DIAPERS

This is a continuation of application Ser. No. 562,906, filed Dec. 19, 1983, abandoned.

TECHNICAL FIELD OF THE INVENTION

This invention relates to disposable diapers, and in particular to an improved adhesive closure system for securing a diaper about the torso of a baby.

BACKGROUND OF THE INVENTION

Disposable diapers provide substantial advantages and convenience over diapers intended to be laundered and reused, and in recent years disposable diapers have met with increased success in the marketplace. Typical disposable diaper structures include a moisture retaining layer of relatively high liquid holding capacity sandwiched between a moisture pervious facing layer and a moisture impervious plastic backing sheet to confine moisture within the moisture retaining layer. Such diapers are shown in U.S. Pat. No. 3,612,055 to Mesek et al. and in U.S. Pat. No. Re: 26,151 to Duncan et al.

Disposable diapers that have been marketed for many years have included adhesive closure systems for convenience in securing the diaper about the torso of a baby. Such adhesive closure systems have typically included separate tape tab members secured to the diaper during manufacture thereof, with the tape tab members having an exposable pressure sensitive adhesive mass thereon which are adhered to the backing sheet of the diaper to retain it in place on the baby. Initially, release sheets were removably secured to the adhesive mass of the tape tabs, to protect the adhesive mass prior to use of the diaper. More recently, a substrate of the tape tabs themselves has been coated with a release material, or otherwise treated to have release properties, with the tape tab being folded to detachably secure the adhesive mass to the release area thereof.

While prior art tape tabs have proven to be convenient to use, and effective in forming a custom fit of the diaper about the torso of an infant, several problems are inherent therein. Not the least of these problems are the added expense that separate tape tabs contribute to the overall cost of the diaper, and difficulties in consistently securing the tape tabs to the diaper by the high speed equipment used to assemble the various diaper components.

As a result of the above problems, it has been recognized by those skilled in the art that it would be desirable to provide an adhesive closure system for disposable diapers which eliminates the need for separate tape tab elements. Typical of such prior art attempts are those shown in U.S. Pat. Nos. 3,638,651 to Torr; 3,840,013 to Mesek et al; 3,848,597 to Endres; and 3,971,380 to Tritsch. For a variety of reasons such prior art attempts have not met with success, and thus the long standing problem remains.

SUMMARY OF THE INVENTION

The present invention provides an improved adhesive closure system for a disposable diaper which eliminates the need for separate tape tab members by providing exposable pressure sensitive adhesive areas directly on the backing layer of the diaper itself, and using such adhesive areas to secure the diaper in place on the baby. The backing layer of the diaper, usually a sheet of polyethylene or the like, is the strongest of the components of the diaper, and by associating the adhesive closure system directly with the backing layer, reliable high strength diaper securement can be consistently obtained. This eliminates one of the most troublesome problems of the prior art, i.e., failure of the so-called "manufacturer's joint" where the separate tape tabs are attached to the diaper.

In accordance with one aspect of the invention the diaper has an hour glass configuration, and the closure means are provided by pressure sensitive adhesive mass sections coated directly on ear portions of the backing sheet that extend outwardly from the facing layer at one end of the diaper. Release means is provided inwardly of the mass coated sections of the backing sheet, so that the closures may be folded inwardly and releasably retained in a storage position. Conveniently, a non-adhesive section is provided on each of the outermost ends of the ear portions of the backing sheet to define finger lift members, which can be manually grasped to fold the closures outwardly from the storage position into a working position for securement of the diaper about the baby's torso.

In one embodiment of the invention the release means is provided on the facing layer adjacent to the adhesive coated section of the ear portion of the backing sheet. In another embodiment of the invention, separable release strips are detachably secured to the ear portions of the backing sheet itself.

BRIEF DESCRIPTION OF THE DRAWINGS

FIG. 1 is a perspective view of a first embodiment of the diaper of the present invention laid out flat and prior to application of the same to a baby, and showing one closure in the storage position and the other closure in the working position;

FIG. 2 is a sectional view taken generally along line 2—2 of FIG. 1;

FIG. 3 is a perspective view of the diaper as applied to a baby;

FIG. 4 is a sectional view taken generally along line 4—4 of FIG. 3;

FIG. 5 is a fragmentary perspective view like FIG. 1, but showing a second embodiment of the diaper of the present invention; and FIG. 6 is an enlarged sectional view taken generally along line 6—6 of FIG. 5.

DESCRIPTION OF THE PREFERRED EMBODIMENTS

While this invention is susceptible of embodiment in many different forms, there is shown in the drawing and will herein be described in detail preferred embodiments of the invention, with the understanding that the present disclosure is to be considered as an exemplification of the principles of the invention and is not intended to limit the invention to the embodiments illustrated. The scope of the invention will be pointed out in the appended claims.

Referring now to the drawings, the disposable diaper 10 of the present invention includes a facing layer 12 formed of a moisture pervious material, and adapted to be positioned adjacent to the infant's skin. Diaper 10 further includes a moisture impervious outer layer 16 substantially coextensive in external dimension with facing layer 12. Sandwiched between outer layers 12 and 16 is an absorbent unit 14 which is smaller in external dimension than outer layers 12 and 16, and which is disposed symmetrically with respect thereto. Absorbent unit 14 may be secured to backing sheet 16 by spaced, parallel glue lines 17, and layers 12 and 16 may be secured to one another outwardly of batt 14 by such glue lines 17, as is well understood by those skilled in the art.

Several different types of materials may be used for facing layer 12, for example, the material may be a nonwoven web made of a mixture of fibers consisting predominantly of inexpensive, short, cellulosic fibers such as short wood pulp fibers or cotton linters in amount of 75 percent to 98 percent, the balance being textile length fibers such as rayon as described in U.S. Pat. No. 3,663,348 to Liloia, et al.

Nonwoven facing materials suitable for use in the forming of diapers of this invention can have fabric weights in the range of from about 0.05 to 5 ounces per square yard and densities of less than 0.15 g/cc., generally in the range of 0.5 to about 0.1 g/cc. The dry strength of the material for a fabric having a weight of about 1.5 ounces per square yard is at least 0.15 lbs. per inch of width in the cross direction. Such fabrics have good elongation, loft, softness, and drape characteristics. Facings may also be made of an apertured nonwoven fabric which is formed, for example, in accordance with the teachings of commonly assigned U.S. Pat. Nos. 2,862,251; 3,081,514; and 3,081,515. Furthermore, facings may also be made from other types of fabric such as those disclosed and described in U.S. Pat. No. 3,485,706 to Evans. Such materials can be made of naturally occurring fibers, synthetic fibers or blends thereof. Typical diaper facings made of polyester type fibers may have a weight of about 0.75 ounces per square yard.

In addition, facings may be made from non-apertured materials such as nonwoven isotropic webs or apertured polyolefin or polyester films having the desired moisture permeability. In all of the aforementioned facings, the materials should be relatively hydrophobic so as to retard wicking within the facing.

A suitable material for backing 16 of the diaper of the present invention can be an opaque polyolefin; for example, polyethylene about 0.001 inch thick. Another suitable material for this purpose is polyethylene terephthalate having a thickness of about 0.005 inch.

Absorbent unit 14 is formed of loosely compacted short cellulose fibers, such as wood pulp fibers or cotton linters, or mixtures thereof which are primarily held together by interfibrous bonds requiring no added adhesive, as is known in the art. Briefly, these batts are a low bulk density coherent web of loosely compacted cellulose fibers preferably comminuted wood pulp fiber in the form of so-called "fluff".

The term "short fibers", as used herein refers to fibers less than about ¼ inch in length, in contrast to "long fibers", or "textile length fibers" which are longer than about ¼ inch in length and generally between ½ and 2½ inches in length.

As is evident from FIG. 1, the illustrated diaper 10 has an hour glass shaped configuration which is provided by cut outs 20 at opposed side marginal edges of the diaper to define a relatively narrow crotch portion in the central section of the diaper and wider waist encircling portions at opposite ends thereof. The waist encircling portions at one end 22 of the diaper define ears or flaps 24 with which the closure means 26 of the present invention are associated. It will be appreciated that the closure means of the present invention may be used with rectangular diapers, as well as those having an hour glass shaped configuration. While absorbent unit 14 has been illustrated as being rectangular, it will be understood that the absorbent unit 14, as well as facing 12 and backing 16, may have an hour glass shape.

With reference to FIG. 1, it will be noted that backing sheet 16 includes ear portions 16a which extend laterally outwardly from an edge 12a of the facing layer at one end of the diaper. Backing layer ear portions 16a include a finger lift tab in the form of a generally rectangularly shaped outermost adhesive free layer 26, a generally rectangularly shaped pressure sensitive adhesive area 28 inwardly of non-adhesive area 27, and a second non-adhesive area 30 inwardly of pressure sensitive adhesive area 28. Pressure sensitive adhesive area 28 may be provided by applying a double faced pressure sensitive adhesive strip to each ear 16a, but it is most preferred that the adhesive area 28 be provided by directly coating an appropriate pressure sensitive adhesive mass directly on ears 16a.

Release means 32 is provided inwardly of adhesive areas 28 for detachably retaining the closure 26 in the storage position illustrated in FIG. 2. Release means 32 may be provided by a treated strip 34 of release paper, as is well known in the art, that is adhered to the outwardly disposed surface of facing layer 12. Alternatively, and preferably, release means 32 is provided by saturating the area of the facing layer adjacent to adhesive area 28 with a suitable release composition.

Referring now to the embodiment of FIGS. 5 and 6, the same reference numerals are used therein to designate elements which are the same as those of the embodiment of FIGS. 1–4. The embodiment of FIGS. 5 and 6 provides the same desirable attributes as the embodiment of FIGS. 1–4 in that it associates closure means 26 directly with ears or flaps 16a of the backing layer 16. However, the embodiment of FIGS. 5 and 6 provides an expanded adhesive area, as compared to the embodiment of FIGS. 1–4, for improved securement of the diaper.

As is most clear from FIG. 6 each ear 16a includes a first adhesive area 28a inwardly of non-adhesive area 27, and a second adhesive area 28b inwardly of adhesive area 28a. Adhesive areas 28a and 28b are illustrated as being contiguous with one another, but it will be understood that adhesive areas 28a and 28b can be separated by a non-adhesive area, if desired.

Each ear 16a is provided with release means 32 inwardly of pressure sensitive area 28a, and in the illustrated embodiment, the release means is provided by a release strip 34a that is removably secured to pressure sensitive adhesive area 28b. As with the embodiment of FIGS. 1–4, the embodiment of FIGS. 5 and 6 includes a non-adhesive area 30 inwardly of pressure sensitive adhesive area 28b. It will be appreciated that when release strip 34a is removed, the entire pressure sensitive area collectively defined by areas 28a and 28b is available for securement of the diaper about an infant. As with the embodiment of FIGS. 1–4, it is preferred that the pressure sensitive adhesive areas 28a and 28b are provided by directly coating a pressure sensitive adhesive mass on ears 16a.

The closure system of the present invention has utility for adult diaper products, as well as for baby diaper products. For baby diaper products, the disposable diaper is applied by laying out the diaper on a single flat surface and placing the baby thereon. The waist underlying end of the diaper is that end having the fastener means and the other end of the diaper extends downwardly between the baby's legs. Next, the downwardly extending edge of the diaper is brought up between the baby's legs to a position covering the perineum and contiguous with the front portion of the baby's waist. The diaper thereafter is secured to the baby by placing the corners of the waist portion of the abdomen covering end as far around the baby's waist as they will go and by bringing the corners of the underlying end of the diaper into an overlapping relationship with the aforementioned corners so that the diaper snugly encircles the baby's waist and provides a custom fit. The adhesive closures are then prepared for use by manually grasping the finger lift tab 27 and unfolding the closure from the storage position to the working position. The diaper is then secured in the desired position by simply urging the pressure-sensitive adhesive surfaces of the backing sheet into contact with the adjacent outer surfaces of the opposite corner of the diaper. Finger-lift tabs 27 provide a readily graspable member which can initiate detachment of the closure when it is desired to remove a soiled diaper.

What is claimed is:

1. A disposable diaper comprising: a moisture pervious facing layer adapted to be positioned adjacent the wearer's body; an absorbent batt adjacent to said facing layer; and a moisture impervious backing layer adjacent to said absorbent batt, said facing and backing layers having a generally hour glass configuration and being larger than said absorbent batt and secured to one another outwardly of said absorbent batt, one end of said backing layer having closure means at opposite sides thereof, said closure means each including a portion of said backing layer extending outwardly of said facing layer, said portions of said backing layer being defined by ears extending outwardly from side marginal edges of said diaper at one end thereof, each of said portions including an adhesive free outer area defining a finger lift tab, said portions of said backing layer each further including a first pressure sensitive adhesive area coated directly thereon inwardly of its adhesive free outer area and a second adhesive area inwardly of the first adhesive area thereof, and release means inwardly of each of said first pressure sensitive adhesive areas, each of said release means being provided on the ear of said backing layer inwardly of said first pressure sensitive adhesive area thereof, each of said release means being defined by release strips releasably associated with said second adhesive area, whereby each of said portions of said backing layer may be folded inwardly to a storage position wherein its first pressure sensitive adhesive area is releasably secured to its associated release means, said portions of said backing layer being folded outwardly from said storage position to a working position by grasping the finger lift tab thereof to expose the pressure sensitive areas thereof for securement of the diaper about the torso of the wearer.

2. A disposable diaper comprising: an hour glass shaped moisture pervious facing layer adapted to be positioned adjacent the wearer's body; an absorbent batt adjacent to said facing layer; and an hour glass shaped moisture impervious backing layer adjacent to said absorbent batt, said facing and backing layers being larger than said absorbent batt and secured to one another outwardly of said absorbent batt, one end of said backing layer having closure means at opposite sides thereof, said closure means each including an ear portion of said backing layer extending outwardly of said facing layer, said ear portions of said backing layer each including an adhesive free outer area defining a finger lift tab, said ear portions of said backing layer each further including a first pressure sensitive adhesive mass inwardly of its adhesive free outer area and coated directly on said ear portions of said backing layer and a second adhesive area inwardly of the first adhesive mass thereof; and release means inwardly of each of said first pressure sensitive adhesive masses, said backing layer inwardly of said first pressure sensitive adhesive mass thereof, said release means being defined by release strips releasably associated with said second adhesive area, whereby each of said ear portions of said backing layer may be folded inwardly to a storage position wherein its first pressure sensitive adhesive mass is releasably secured to its associated release means, said ear portions of said backing layer being folded outwardly from said storage position to a working position by grasping the finger lift tab thereof to expose the pressure sensitive masses thereof for securement of the diaper about the torso of the wearer.

* * * * *